United States Patent [19]

Kagotani

[11] Patent Number: 4,937,081

[45] Date of Patent: Jun. 26, 1990

[54] PROCESS FOR PRODUCING POROUS, SPHERICAL PARTICLES

[75] Inventor: Masahiro Kagotani, Himeji, Japan

[73] Assignee: Daicel Chemical Industries Ltd., Osaka, Japan

[21] Appl. No.: 144,042

[22] Filed: Jan. 14, 1988

[51] Int. Cl.$^5$ ................................................ A61K 9/16
[52] U.S. Cl. ..................................... 424/498; 424/489; 424/499
[58] Field of Search ........................ 424/499, 498, 489; 264/5, 9

[56] References Cited

U.S. PATENT DOCUMENTS

| | | | |
|---|---|---|---|
| 2,805,977 | 9/1957 | Robinson et al. | 424/499 |
| 2,921,883 | 1/1960 | Reese et al. | 424/498 X |
| 3,082,154 | 3/1963 | Allan | 424/498 |
| 3,228,257 | 6/1967 | Vrancken et al. | 264/5 |
| 4,089,800 | 5/1978 | Temple | 264/5 X |
| 4,151,274 | 4/1979 | Schlueter et al. | 264/5 X |
| 4,221,862 | 9/1980 | Naito et al. | 264/5 X |

FOREIGN PATENT DOCUMENTS

| | | | |
|---|---|---|---|
| 0037740 | 10/1981 | European Pat. Off. | 424/498 |
| 62-115031 | 5/1987 | Japan | 264/9 |

Primary Examiner—Thurman K. Page
Attorney, Agent, or Firm—Bryan, Cave, McPheeters & McRoberts

[57] ABSTRACT

A process for producing porous, spherical particles of cellulose fatty acid esters which comprises dissolving a cellulose fatty acid ester and a gelling agent therefor in an organic solvent, adding the solution thus obtained to an aqueous medium with stirring to form droplets, converting said droplets to gel particles of cellulose fatty acid ester in the presence or absence of a gelation accelerator, and separating porous, spherical particles of cellulose fatty acid ester.

11 Claims, No Drawings

PROCESS FOR PRODUCING POROUS, SPHERICAL PARTICLES

BACKGROUND OF THE INVENTION

1. Field of the Invention

This invention relates to a process for producing porous, spherical particles of cellulose fatty acid esters. The spherical particles produced by the process of this invention are excellent in particle size uniformity, sphericity and porosity, and can be saponified into spherical particles of cellulose. Both of them are useful as column packing materials for chromatography and additives or excipients for various other purposes.

2. Description of the Prior Art

Fine particles of polymers have been used as additives for plastics, excipients for medical preparations and antiblocking agents, and in many other fields such as cosmetic and printing industries. Recently, these are receiving attention also as carriers to immobilize enzymes and microorganisms, and as packing materials for chromatography. Of various types of polymers, cellulose fatty acid esters, which are particularly soluble in organic solvents and can be easily converted into fine particles, have been extensively used for the purposes mentioned above. In addition, it is also possible to convert the fine particles of cellulose fatty acid esters into particles of cellulose by hydrolysis, or to introduce other functional groups (for example, ion-exchangeable groups) into the molecules of cellulose fatty acid ester, for specific application.

Methods have previously been proposed for the manufacture of spherical particles. For example, a cellulose fatty acid ester may be dissolved in a low-boiling chlorinated hydrocarbon (e.g., dichloromethane), or a solvent mixture containing the same as the main component, the solution thus obtained subjected to dry spinning, and the filaments formed cut into chips, which are then melted by heating in a high-boiling medium (e.g., silicone oil), thus giving spherical particles of the cellulose fatty acid ester. In another method, the solution prepared above is added to an aqueous medium with stirring to form droplets, the resulting dispersion is heated to evaporate the solvent from the droplets, and the spherical particles of cellulose fatty acid ester thus prepared are then saponified into particles of cellulose. [Japanese Patent Publication No. 39565 and No. 40618 (1980)]

These methods, however, involve many steps and consume much energy. Furthermore, the particles of cellulose fatty acid ester obtained are relatively dense in structure, and hence the resulting particles of cellulose are also dense, with the porosity being too low for use as the packing materials for chromatography and for use in sustained release drugs.

The following methods have also been proposed to obtain spherical particles of high porosity. For example, a cellulose fatty acid ester may be dissolved in a low-boiling chlorinated hydrocarbon, or a solvent mixture containing the same as the main component, together with a water-soluble polymer that differs in solubility in the chlorinated hydrocarbon solvent from the cellulose fatty acid ester. The solution thus prepared is added to an aqueous medium with stirring to form droplets, the resulting dispersion is heated to evaporate the solvent from the droplets, and the spherical particles of cellulose fatty acid ester thus prepared are then saponified and freed from the water-soluble polymer, giving spherical particles of cellulose. [Japanese Patent Kokai No. 55055 (1979)] In another method, a high-boiling solvent, such as a higher aliphatic alcohol of 6 to 18 carbon atoms (for example, n-octanol), is added when dissolving the cellulose fatty acid ester in the low-boiling chlorinated hydrocarbon or a solvent mixture containing the same as the main component. The solution thus prepared is added to an aqueous medium with stirring to form droplets, and the resulting dispersion is heated to evaporate the low-boiling solvent from the droplets. The spherical particles of cellulose fatty acid ester containing the high-boiling solvent thus prepared are then saponified and freed from the high-boiling solvent, giving spherical particles of cellulose. [Japanese Patent Kokai No. 24429 (1981)]

In the latter method, in which the low-boiling solvent is removed from droplets by heating, the size of the pores in the porous particles, as well as the diameter, density and other properties of the particles, tend to vary because of the thermoplasticity of cellulose fatty acid esters, thus requiring complex process control to obtain final products of consistent quality. In the former method, in which the water-soluble polymer is removed from the droplets by washing, a high porosity can be achieved but the sizes of individual pores are rather large and their number is limited. Such porous particles containing rather large pores may be used as the carrier to immobilize enzymes and microorganisms and as the starting material for the manufacture of ion-exchangeable cellulose derivatives, but are not suitable as, the packing materials for chromatographic separations of proteins and enzymes.

SUMMARY OF THE INVENTION

We have found that cellulose fatty acid esters, upon gelation under proper conditions, form a relatively stable, space network structure and are hence suitable for the formation of a large number of micropores. This invention was accomplished based on these findings.

This invention provides a process for producing porous, spherical particles which comprises dissolving a cellulose fatty acid ester and a gelling agent therefor in an organic solvent, adding the solution thus obtained to an aqueous medium with stirring to form droplets, converting said droplets to gel particles of cellulose fatty acid ester in the presence or absence of a gelation accelerator, and separating porous, spherical particles of cellulose fatty acid ester.

DESCRIPTION OF THE PREFERRED EMBODIMENTS

The cellulose fatty acid esters used in this invention may be any fatty acid esters of cellulose that are insoluble in water and are capable of regenerating cellulose by saponification. As illustrative examples may be mentioned cellulose acetates, cellulose propionates and cellulose butyrates with a degree of substitution of 1.0 or more, but cellulose diacetate and cellulose triacetate are particularly suitable for practical application.

Any known organic solvents may be used if they can dissolve cellulose fatty acid esters; halogenated hydrocarbons such as dichloromethane and chloroform, and mixtures thereof with about 5 to 20 volume % of a lower aliphatic alcohol of 1 to 5 carbon atoms such as methanol, ethanol and isopropanol, show high solubility for cellulose fatty acid esters and are advantageous for the purpose of this invention. There is no specific limitation upon the amount of cellulose fatty acid ester dissolved in these solvents, but a concentration in the range of about 3 to 15 weight % is preferable.

As examples of the gelling agents to be added to the solution of cellulose fatty acid esters, there may be mentioned higher aliphatic carboxylic acids, such as oleic, lauric, myristic, palmitic, stearic, behenic, isostearic and n-octanoic acids; higher aliphatic alcohols having at least 6 carbon atoms, such as n-hexanol, n-heptanol, n-octanol, decyl alcohol, tridecanol, 2-ethylhexanol and n-nonanol; and aliphatic esters of aromatic carboxylic acids, such as butyl benzoate, hexyl benzoate, monobutyl phthalate, monooctyl phthalate, dibutyl phthalate, dioctyl phthalate, diethyl phthalate, dilauryl phthalate, butyl benzyl phthalate, diheptyl phthalate and dicyclohexyl phthalate. Suitably, amount of these gelling agents to be added is in the range from 5 to 50% based on the volume of halogenated hydrocarbon used, preferably in the range of about 5 to 20%.

A solution of a cellulose fatty acid ester and a gelling agent as mentioned above in an aforementioned solvent is added to an aqueous medium with stirring to form droplets of said solution. As examples of the aqueous mediums herein used, may be mentioned aqueous solutions containing a water-soluble polymer (e.g., gelatin, CMC and PVA), or water to which a surface-active agent and a defoaming agent are added in a small amount. These chemicals are added to stabilize the droplets formed, and the suitable amount is 1 to 5 weight % of water. The cellulose fatty, acid ester contained in the droplets dispersed in the aqueous medium gradually gels, thus forming gel particles. This gelation can be significantly accelerated by addition of a gelation accelerator after the droplets are formed. As the gelation accelerator, compounds may be used which are freely miscible with water and moderately soluble in the halogenated hydrocarbon solvent. These include lower alcohols such as methanol, ethanol and isopropanol; ketones such as methyl ethyl ketone; ethers such as tetrahydrofuran and dimethoxyethane; and carboxylic acids such as acetic acid. Of these, lower alcohols are the most preferred because of the ease of handling. The suitable amount to be added is about 0.2 to 2 times the volume of the aqueous medium, but should be reduced with increasing amount of gelling agent. Gelation of cellulose fatty acid esters proceeds slowly even in the absence of a gelation accelerator. In this case, gelation can be accelerated by increasing the amount of the gelling agent, for example, to more than 10 % based on the volume of halogenated hydrocarbon solvent. However, the larger the amount of the gelling agent, the larger the amount of the solvent required to remove the gelling agent from the formed beads.

The amount of lower alcohol used as the gelation accelerator is larger than that used as a co-solvent with the halogenated hydrocarbon. The same type of lower alcohol may be employed for both purposes, and this is more advantageous than the use of different types of alcohols because of the ease of solvent recovery in the subsequent step.

The gel particles thus formed are then freed from the solvent, gelling agent and gelation accelerator in the usual way. For example, the particles are washed with water, the solvent, gelling agent and gelation accelerator contained therein are displaced with a suitable solvent (e.g., the lower alcohol used as a component of solvent mixture), and this solvent is then displaced with water, giving porous spherical particles of a cellulose fatty acid ester having a large number of micropores and excellent sphericity and particle size uniformity.

The size of spherical particles of cellulose fatty acid esters prepared by the process of this invention is dictated by the size of droplets formed in the preceding step, because normally one particle is produced from one droplet. The size of droplets formed in the aqueous medium is dependent on the agitation efficiency while the organic solution of cellulose fatty acid ester is being added to the aqueous medium. The higher the agitation efficiency, the smaller will be the size of droplets. And when the concentration of cellulose fatty acid ester in the solution is lower, the agitation efficiency is higher with the same speed of the agitator because of the lower viscosity of the solution, thus giving smaller droplets. The concentration of cellulose fatty acid ester is also a factor that governs the porosity of particles; the lower the concentration, the higher will be the porosity.

Described below is the mechanism for the formation of porous spherical particles of a cellulose fatty acid ester when a mixture of chloroform and isopropanol is used as the organic solvent.

A solution of cellulose fatty acid ester and a gelling agent in chloroform/isopropanol solvent mixture is added to an aqueous medium at room temperature with stirring to form droplets in said solution. A large amount of isopropanol is then added to the resultant aqueous dispersion to displace the chloroform in each droplet, with the result that gelation takes place by the action of the gelling agent involved, forming gel particles with network structure. The particles thus obtained are an elastic solid which deforms when pressed with the fingers and is restored to its original form when the applied force is released. These particles are recovered from the aqueous medium and treated with an appropriate solvent to remove the gelling agent and remaining chloroform, yielding particles of the cellulose fatty acid ester having a porous structure.

The porous particles of cellulose fatty acid ester thus obtained can be saponified in the usual way (for example, by the use of sodium hydroxide) into porous particles of cellulose having excellent properties similar to the above particles.

Porous spherical particles of cellulose fatty acid esters can be simply produced by the process of this invention at low cost and with high reproducibility. In the conventional methods, the properties of the final particles are influenced by the temperature conditions when the low-boiling solvent is removed. In the process of this invention, on the contrary, particles having a large number of micropores and excellent sphericity and particle size uniformity can be obtained with high reproducibility, if the solvent composition, the concentrations of cellulose fatty acid ester and gelling agent, and stirring condition in the step of particle formation are properly set.

Such particles can be prepared without using any gelation accelerator, but use of an accelerator helps reduce the time required for gelation and washing with a relatively smaller amount of gelling agent.

The particles of cellulose fatty acid esters prepared by the process of this invention can be used as column packing materials for gel filtration chromatography, etc., anti-blocking agents, additives for plastics and soil conditioners. The particles of cellulose derived therefrom by saponification also contain a large number of micropores and are suitable for use as cosmetic materials, column packing materials for gel filtration chromatography, etc., and carriers in sustained release medical preparations. In particular, chemical modification of the cellulose particles gives products which can be used as carriers for ion-exchange and affinity chromatography.

The following Examples further illustrate the invention but are not intended to limit its scope.

Examples 1 through 3 describe the cases in which a gelation accelerator is used, while no accelerator is used in Examples 4 and 5. Comparative Example 1 is similar to Example 1 except that no gelling agent is used, and Comparative Example 2 is similar to Example 4 except that no gelling agent is used.

EXAMPLE 1

To a solution of 25 g cellulose triacetate (acetylation degree: 61%; product of DAICEL CHEMICAL INDUSTRIES, LTD., in Japan; it is referred to as DAICEL hereinafter) in 200 ml chloroform containing 25 ml isopropanol, was added a mixture of 25 ml dibutyl phthalate and 75 ml chloroform, and the resulting clear solution was dispersed in 2 liters of 1% aqueous solution of gelatin containing 0.5 g of a defoaming agent (Antifoam E-20; product of Kao Corporation in Japan) while stirring the mixture at a revolution speed of 700 rpm over a period of 0.5 hour. After lowering the revolution speed of agitator to 300 rpm, 1 liter of isopropanol was slowly added to the dispersion, and it was observed that the droplets of chloroform/dibutyl phthalate containing cellulose triacetate began to coagulate. The beads of cellulose triacetate gel thus formed were collected by filtration, thoroughly washed with water, and dispersed in 1 liter of isopropanol to displace the chloroform and dibutyl phthalate in the droplets with isopropanol. The treated beads were collected by filtration, washed with 0.5 l isopropanol, dispersed in water, and heated at about 70° C. to displace the isopropanol in the beads with water. The beads of cellulose triacetate thus obtained were collected by filtration and thoroughly washed with water (volume: 250 ml; particle size under wet condition: about 50 to 250 μm). Observation under an optical microscope revealed high sphericity of these particles.

Classification under wet condition gave 130 ml of particles 75 to 150 μm in size and 100 ml of particles 150 to 250 μm in size.

The beads of cellulose triacetate obtained above [75 to 150 μm in size; 100 g (wet)] was mixed with 300 ml of 75% ethanol and 600 ml of 1N NaOH solution, and the mixture was stirred at room temperature for 24 hours to effect hydrolysis. Neutralization of the reaction mixture with dilute acetic acid, followed by thorough washing with water, yielded particles of cellulose. The density of these cellulose particles—cellulose density (CD)—was measured according to the method described below, and the result obtained was 15%.

The cellulose beads obtained above were evaluated as packing material for gel-filtration column chromatography. The exclusion limit of measurable molecular weight was about 40,000 for dextran molecules.

The cellulose beads were found to be particles of high sphericity when observed under an optical microscope.

High sphericity was also observed with all the gel particles and cellulose beads obtained in the following Examples.

Measurement of CD

A swollen sample of cellulose particles is filled in a glass column 8 mm in inside diameter to a height of about 10 cm, and the volume of the particles, $V_0$, is calculated as follows:

$$V_0 = (0.4)^2 \pi h$$

wherein h is the height of cellulose particles packed in the column (cm).

Blue dextran with molecular weight of 2,000,000 (in the form of 0.5% aqueous solution) is then added to the column to move down the water present in the space among the particles, thus measuring its volume ($V_t$ ml; dead volume). The cellulose particles are taken out from the column, collected by filtration and thoroughly washed with water and dried, and the dry weight, W(g), is measured. The density can be calculated from the following equation:

$$CD(\%) = \frac{W}{V_0 - V_t} \times 100$$

COMPARATIVE EXAMPLE 1

(Similar to Example 1 Except That No Dibutyl Phthalate Is Added)

A solution of 26 g cellulose triacetate (acetylation degree: 61%; product of DAICEL) in 275 ml chloroform containing 25 ml isopropanol was dispersed in 2 liters of 1% aqueous solution of gelatin containing 0.5 g of a defoaming agent (Antifoam E-20) while stirring the mixture at a revolution speed of about 700 rpm over a period of 0.5 hour. After lowering the revolution speed of agitator to 300 rpm, 1 liter of isopropanol was slowly added to the dispersion. No coagulation of droplets took place; instead, the droplets coalesced to form a lump of cellulose triacetate, failing to produce any beads.

EXAMPLE 2

To a solution of 25 g cellulose triacetate (acetylation degree: 61%; product of DAICEL) in 200 ml chloroform containing 25 ml isopropanol, was added a mixture of 25 ml oleic acid and 75 ml chloroform, and the mixture was stirred for some time. The resulting clear solution was dispersed in 2 liters of 1% aqueous solution of gelatin containing 2 g of a surface-active agent (Monogen-uni; product of DAI-ICHI KOGYO SEIYAKU CO., LTD., in Japan) and 1 g of a defoaming agent (Antifoam E-20) while stirring the mixture at a revolution speed of about 700 rpm over a period of 0.5 hour. After lowering the revolution speed of agitator to 300 rpm, 1 liter of isopropanol was slowly added to the dispersion, giving spherical gel particles of cellulose triacetate.

The particles, recovered in the same manner as in Example 1, were found to be spherical in shape with the size ranging from 75 to 250 μm. Particles 75 to 150 μm in size were collected by classification and saponified in the same way as in Example 1, giving cellulose beads. The CD value of the beads thus obtained was 18%.

EXAMPLE 3

To a solution of 20 g cellulose triacetate (acetylation degree: 61%; product of DAICEL) in 250 ml chloroform containing 20 ml isopropanol, was added a mixture of 30 ml dibutyl phthalate and 120 ml chloroform, and the mixture was stirred for some time. The resulting clear solution was dispersed in 2 liters of 1% aqueous solution of gelatin containing 2 g of a surface-active agent (Monogen-uni) and 1 g of a defoaming agent (Antifoam E-20) while stirring the mixture at a revolution speed of about 700 rpm. After lowering the revolution speed of agitator to 300 rpm, 1 liter of isopropanol was slowly added to the dispersion, giving spherical gel particles of cellulose triacetate. Treatment in the same manner as in Example 1 yielded about 300 ml of porous spherical particles 20 to 100 μm in size. Particles 20 to 50 μm in size were collected by classification and saponified in the same way as in Example 1, giving cellulose beads. The CD value of the beads thus obtained was 12%.

EXAMPLE 4

To a solution of 25 g cellulose triacetate (acetylation degree: 61%; product of DAICEL) in 170 ml dichloromethane containing 30 ml methanol, was added a mixture of 50 ml dibutyl phthalate and 30 ml dichloromethane, and the mixture was stirred for some time. The resulting clear solution was dispersed in 0.5 liter of 1% aqueous solution of gelatin containing 1 g of a defoaming agent (Antifoam E-20) while stirring the mixture at a revolution speed of about 7500 rpm. The dispersion thus obtained was slowly added to 1 liter of 1% aqueous solution of gelatin, and stirring was continued for one hour. After standing for some time, the supernatant was removed, 1 liter of a 1:1 water/isopropanol mixture was added to the residue, and stirring was continued for some time longer for washing. The beads of cellulose triacetate were collected by filtration, thoroughly washed with water and dispersed in 1 liter of isopropanol, and the dispersion was heated at 70° to 80° C. for 2 to 3 hours with stirring. The treated beads were collected by filtration, washed twice with 0.5 liter of isopropanol, and dispersed in water. The aqueous dispersion was then heated at 80° C. for two hours, followed by filtration and thorough washing with water. Classification of the product obtained under wet condition yielded 10 ml of particles 10 to 30 μm in size, 40 ml of particles 30 to 75 μm in size, 80 ml of particles 75 to 150 μm in size and 20 ml of particles 150 to 250 μm in size. Classified particles (75 to 150 μm in size; 100 g) were then mixed with 300 ml of 75% ethanol and 600 ml of 1N NaOH solution, and the mixture was stirred at room temperature for 24 hours to effect hydrolysis. The resulting mixture was neutralized with dilute acetic acid, and the beads of cellulose thus formed were collected by filtration and thoroughly washed with water. The CD value measured by the aforementioned method was 32%.

The cellulose beads obtained above were evaluated as packing material for gel-filtration column chromatography. The maximum measurable molecular weight was about 20,000 for dextran molecules.

COMPARATIVE EXAMPLE 2

(No Gelling Agent Added)

A solution of 25 g cellulose triacetate (acetylation degree: 61%; product of DAICEL) in 200 ml dichloromethane containing 30 ml methanol was dispersed in 0.5 liter of 1% aqueous solution of gelatin containing a defoaming agent (Antifoam E-20) while stirring the mixture at a revolution speed of 7500 rpm, the resulting dispersion was slowly added to 1 liter of 1% gelatin solution with stirring, and stirring was continued for an additional one hour. When the dispersion was treated in the same manner as in Example 1, coalescence of the droplets took place to form a lump of cellulose triacetate, failing to produce any beads.

EXAMPLE 5

To a solution of 25 g cellulose triacetate (acetylation degree: 61%; product of DAICEL) in 170 ml dichloromethane containing 30 ml methanol, was added a mixture of 50 ml oleic acid and 30 ml dichloromethane, and the mixture was stirred for some time. The resulting clear solution was dispersed in 0.5 liter of 1% aqueous solution of gelatin containing a defoaming agent (Antifoam E-20) while stirring the mixture at a revolution speed of about 7500 rpm. The dispersion thus obtained was slowly added to 1 liter of 1% aqueous gelatin solution with stirring, and stirring was continued for about one hour. Treatment in the same manner as in Example 4 gave particles of cellulose triacetate similar to those in Example 4. Hydrolysis of classified particles 75 to 150 μm in size yielded beads of cellulose having a CD value of 30%.

What is claimed is:

1. A process for producing porous spherical particles of cellulose fatty acid esters, which comprises:
   (a) dissolving a cellulose fatty acid ester in a mixture of a halogenated hydrocarbon in which the cellulose ester is soluble, a gelling agent and a lower aliphatic alcohol having from 1 to 5 carbon atoms, said ester being insoluble in water and capable of regenerating cellulose by saponification and said alcohol being miscible with water;
   (b) adding the resulting solution to an aqueous medium with stirring to form droplets of the cellulose ester;
   (c) converting the droplets to gel particles of the cellulose ester having a network structure; and
   (d) separating porous, spherical particles of the cellulose ester.

2. The process of claim 1 wherein the cellulose fatty acid ester is cellulose triacetate.

3. The process of claim 1 wherein a gelation accelerator is present and is used in an amount of 0.2 to 2 times the volume of the aqueous medium.

4. The process of claim 1 wherein the halogenated hydrocarbon is dichloromethane or chloroform.

5. The process of claim 4, wherein the organic solvent is said halogenated hydrocarbon containing 5 to 20 volume % of said lower aliphatic alcohol.

6. The process of claim 1 wherein the cellulose fatty acid ester is used in an amount of about 3 to 15% based on the weight of the organic solvent.

7. The process of claim 1 wherein the gelling agent is a higher aliphatic carboxylic acid, a higher aliphatic alcohol having at least 6 carbon atoms, or an aliphatic ester of an aromatic carboxylic acid.

8. The process of claim 7, wherein the higher aliphatic carboxylic acid is oleic, lauric, myristic, palmitic, stearic, behenic, isostearic or n-octanoic acid; the higher aliphatic alcohol is n-hexanol, n-heptanol, n-octanol, decyl alcohol, tridecanol, 2-ethylhexanol or n-nonanol; and the aliphatic ester of aromatic carboxylic acid is butyl benzoate, hexyl benzoate, monobutyl phthalate, monooctyl phthalate, dibutyl phthalate, dioctyl phthalate, diethyl phthalate, dilauryl phthalate, butyl benzyl phthalate, diheptyl phthalate or dicyclohexyl phthalate.

9. The process of claim 7, wherein the gelling agent is dibutyl phthalate.

10. The process of claim 1 wherein the gelling agent is used in an amount of about 5 to 50% based on the volume of the halogenated hydrocarbon.

11. The process of claim 1 wherein a gelation accelerator is present and is a lower aliphatic alcohol of 1 to 5 carbon atoms.

* * * * *